(12) United States Patent
Call et al.

(10) Patent No.: US 6,267,016 B1
(45) Date of Patent: Jul. 31, 2001

(54) IMPACT PARTICULATE COLLECTOR USING A ROTARY IMPELLER FOR COLLECTING PARTICULATES AND MOVING A FLUID

(75) Inventors: Patrick T. Call, Richland; Vanessa M. Kenning, Kennewick; Charles Call, Pasco; Joseph G. Birmingham, Richland; Donald J. Hammerstrom, W. Richland, all of WA (US)

(73) Assignee: MesoSystems Technology, Inc., Kennewick, WA (US)

( * ) Notice: Subject to any disclaimer, the term of this patent is extended or adjusted under 35 U.S.C. 154(b) by 0 days.

(21) Appl. No.: 09/265,619

(22) Filed: Mar. 10, 1999

(51) Int. Cl.$^7$ .................................................. G01N 31/20
(52) U.S. Cl. .................................................. 73/863.22
(58) Field of Search ......................... 73/863.21, 863.22, 73/28.05, 28.06; 210/781, 780, 194, 196, 197, 360.1, 380.1; 55/340; 95/267, 269

(56) References Cited

U.S. PATENT DOCUMENTS

| | | | |
|---|---|---|---|
| 3,518,815 | * 7/1970 | McFarland et al. | 73/863.22 |
| 3,891,550 | * 6/1975 | Gray et al. | 210/780 |
| 5,201,231 | * 4/1993 | Smith | 73/863.22 |
| 5,421,214 | * 6/1995 | Burgdorfer | 435/309.1 |
| 5,437,198 | * 8/1995 | John | 73/863.22 |
| 5,693,895 | * 12/1997 | Baxter | 73/863.22 |

* cited by examiner

Primary Examiner—Robert Raevis
(74) Attorney, Agent, or Firm—Ronald M. Anderson

(57) ABSTRACT

A particle collector includes a combined impact collector and fan, which is usable for both drawing air or other gaseous fluid in which particulates are entrained into a cavity, and then separating the particulates from the gaseous fluid by providing a rotating surface that impacts the particulates. The particulates also impact on other surfaces within the cavity, including its inner surface, and are washed from these surfaces, which are wetted with water or other liquid injected into the cavity. The cavity is defined by a housing having an inlet port through which the air or other gaseous fluid is drawn. The combined impact collector and fan includes a plate on which a plurality of spaced-apart impeller vanes are disposed. The shape of the impeller vanes produces a centrifugal fan effect when they are rotated within the cavity. The water or other liquid is either continuously or intermittently injected into the cavity to wash the particulates from the impeller vanes and other surfaces on which they have impacted. The particulates are carried by the liquid through a threaded drain port, into a receiver that includes an exhaust port for the air or gaseous fluid. A pump recirculates the liquid from the receiver through a conduit that sprays the liquid into the cavity through the inlet port. The particulates collected in the receiver provide a specimen that can be analyzed to detect or identify the particulates that were entrained in the air or other gaseous fluid.

42 Claims, 6 Drawing Sheets

Figure 1:
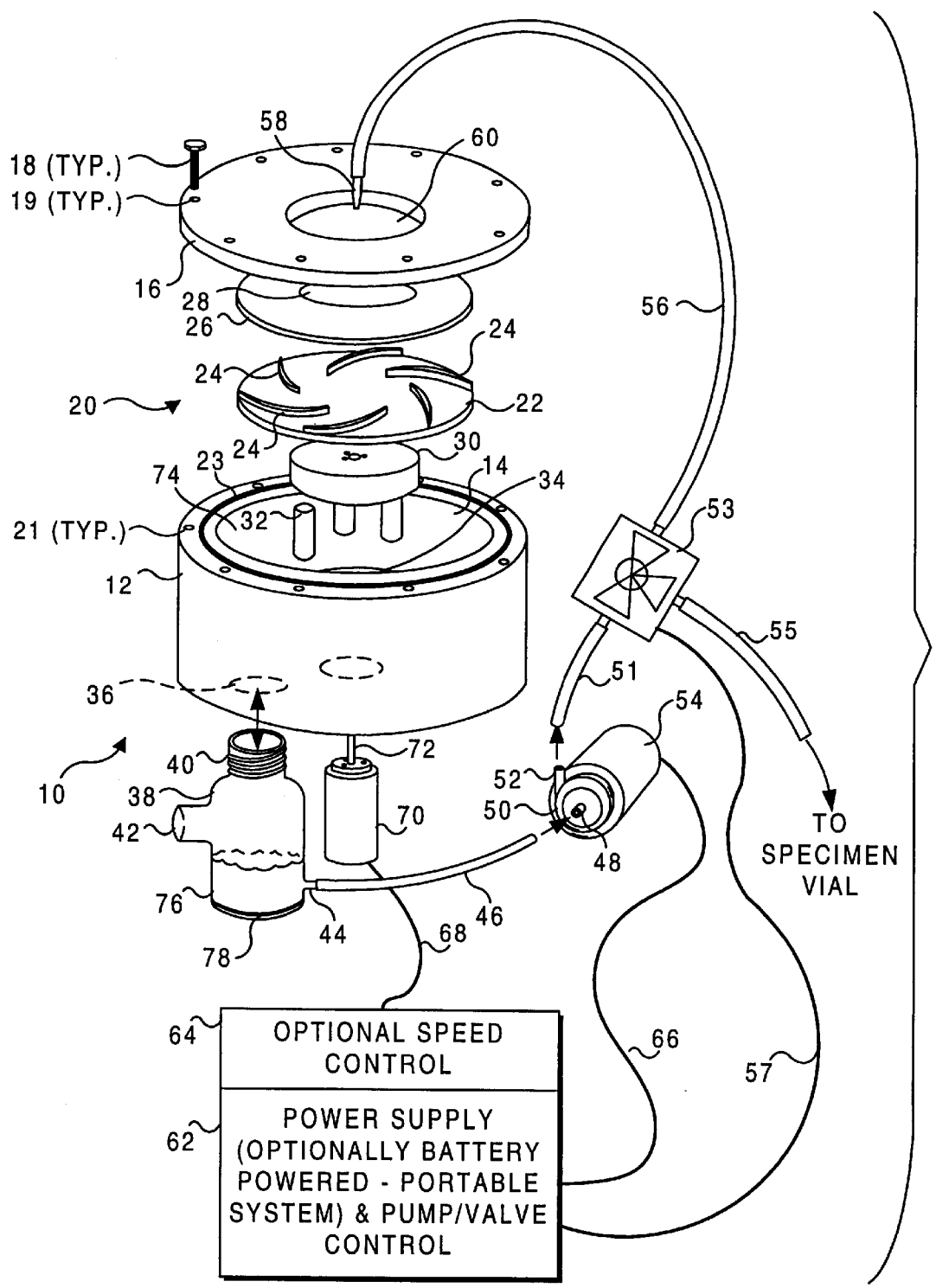

IMPACT PARTICULATE COLLECTOR USING A ROTARY IMPELLER FOR COLLECTING PARTICULATES AND MOVING A FLUID

GOVERNMENT RIGHTS

This invention was made under contract with the United States Department of Defense, under Contract No. DAAM01-97-C-0036, and the United States government may have certain rights in the invention.

FIELD OF THE INVENTION

This invention generally relates to an impact collector, and more specifically, to an impact collector that employs a rotating member to collect particulates from a gaseous fluid that is caused to flow toward the rotating member.

BACKGROUND OF THE INVENTION

It is often necessary to separate particulates from air or other gaseous fluids in which the particulates are entrained. For example, aerosols comprising small droplets of liquid dispersed into air are not easily analyzed unless the aerosol materials are separated from the air to produce a more concentrated sample that can then be analyzed. The aerosols or particulates can be liquids, solids, or semi-solids that are sufficiently small to be dispersed within and carried about in air and may include inorganic or organic chemicals, or living materials, e.g., bacterial cells or spores. Also, solids or semi-solids can be introduced into a liquid that is then dispersed within air as an aerosol mist so that the solids are carried within the liquid droplets comprising the aerosol mist.

Generally, it is difficult to identify materials comprising particulates entrained in a gaseous fluid unless the particulates can be collected by separating them from the air or other gaseous fluid and concentrated in a specimen suitable for analysis. In addition to identifying the type of particulates entrained in a gaseous fluid, it may be important to classify the size of the particulates. For example, when checking stack emissions, it is usually important to determine the materials carried as particulates within the emissions and the size of the particulates to determine whether the emissions conform to pollution control limits.

Particle impact devices are commonly used for collecting particulates from gaseous streams in which they are dispersed. Conventional particle impactors employ circuitous paths with many abrupt changes of direction along the passages through which a particulate laden fluid flows. The particulates, being substantially more massive than the molecules of the fluid in which they are entrained, fail to negotiate the abrupt turns in these passages and are thus separated from the moving fluid stream, collecting on the surfaces that they impact. To function properly, such prior art particle impactors require that the gaseous fluid stream be moved through the impactor at least at some minimum velocity. Typically, a separate fan is used to provide the required velocity to the fluid flowing into the particle impactor. One problem with such particle impactors of this type is that it is often difficult to separate the particulates collected by such particle impactors from the surfaces on which they have impacted. Furthermore, many of the particulates do not collect on the desired surfaces and are therefore unavailable for analysis and evaluation.

Another type of prior art particle impactor includes a rotating arm that is placed with flow of a fluid in which particulates are entrained. A separate fan is employed to move the fluid into the vicinity of the rotating arm. The particulates impacting the rotating arms are separated from the fluid. However, such collectors do not provide a simple and efficient mechanism to remove the particulates from the rotating arms.

Virtual impactors are another type of prior art device used for separating particulates from a gaseous fluid, again using the differences in mass of the particulates and the fluid molecules to facilitate the separation process. In this type of device, the gaseous fluid is directed along a passage and separated by a divider disposed within the passage into a fast moving major stream and a much slower moving minor stream. The more massive particulates remain in the slower moving minor stream, while the fluid and very small particulates continue through the device in the major stream. However, virtual impactors simply separate the streams, but do not provide a specific collection mechanism for separating the particulates from the fluid in which they are carried. Again, a separate fan or blower mechanism is employed to impart the required velocity to the fluid moving through the virtual impactor.

Although other types of particle impactors and virtual impactors are described in the prior art, none of them employ a single element for both moving the gaseous fluid in which particulates are entrained and providing a specific surface on which the particulates are collected as a result of their impact with that surface. Further, none of these prior art devices provide an efficient mechanism for actually collecting a concentrated specimen comprising the particulates separated from the gaseous fluid in which they were entrained. Clearly, it would be desirable to produce a compact particulate impactor for use in a portable device designed to collect a specimen of the particulates and to facilitate identification and analysis of the particulates carried by the gaseous fluid. Such a device should be capable of directly moving the gaseous fluid and particulates into the collector at a required velocity without use of a separate fan or blower, and provide a specimen containing the particulates once they have been separated from the gaseous fluid stream by impacting on a surface. It will be apparent that a miniaturized particle impactor of this type would be of considerable value in portable, hand-carried field apparatus used, for example, to identify bacteriological or chemical warfare agents that have been dispersed as an aerosol. Prior art particle impactors do not provide these features and functions.

SUMMARY OF THE INVENTION

In accord with the present invention, apparatus is defined for separating particulates from a fluid in which the particulates are entrained. The apparatus includes a housing defining a port through which the fluid carrying the particulates passes. In one embodiment, an electrically energizable motor that rotates a drive shaft is included for rotatably driving a combined impact collector and fan that is mechanically coupled to the drive shaft. The combined impact collector and fan is disposed within a cavity defined by the housing. Rotation of the combined impact collector and fan draws the fluid carrying the particulates into the cavity of the housing through the port, so that no other fan is required to move the fluid into the cavity. The particulates in the fluid impact the rotating combined impact collector and fan, are retained thereon, and are thus separated from the fluid.

Also included is a conduit that conveys a liquid into the cavity of the housing. The liquid is directed toward the combined impact collector and fan, washing away the particulates that have impacted thereon and which were thus separated from the fluid and retained on the combined impact collector and fan. A passage is formed in the housing and is in fluid communication with a receiver. The liquid washing the particulates from the combined impact collector and fan is radially dispersed onto an inner surface of the housing and flows into the receiver through the passage.

In one application of the present invention, the particulates comprise droplets. A concentration of the matter comprising the droplets in the liquid thus becomes increasingly greater within the receiver and is substantially greater than within the fluid drawn into the cavity. In another application of the present invention, the particulates comprise either a solid or a semi-solid. If sufficiently more dense than the liquid, these particulates substantially settle out of the liquid within the receiver.

The apparatus preferably includes a pump that draws the liquid from the receiver and circulates it back into the cavity of the housing through the conduit. The pump is preferably mechanically coupled to the shaft of the electrically energizable motor and is driven by it. Alternatively, the pump may be driven by a different motor. A power supply is included to provide an electrical current to the electrically energizable motor. In one embodiment, the power supply includes a battery that produces the electrical current. Also, the power supply and the housing are portable and sufficiently small in size and weight to be readily hand carried. This embodiment is thus useful for collecting particulates in the field.

The combined impact collector and fan is preferably coated with a substance to which the particulates readily adhere when the substance is dry. However, when wetted with the liquid, the particulates are released from the combined impact collector and fan. Another alternative coating is characterized by having a low coefficient of friction, so that the particulates that are separated from the fluid by striking the combined impact collector and fan are readily released therefrom and are carried away with the liquid.

Another aspect of the present invention is directed to a method for separating particulates from a fluid. This method includes steps that are generally consistent with the functions of the elements of the apparatus discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1 is an exploded isometric view of a first embodiment of a particle impactor in accord with the present invention;

FIG. 2 is a cross-sectional elevational view of the first embodiment shown in FIG. 1;

FIG. 3 is a cross-sectional elevational view of a second embodiment of a particle impactor in accord with the present invention;

FIG. 4 is a plan view of a combined impact collector and fan used in both embodiments of the present invention;

FIG. 5 is a plan view of a portion of the combined impact collector and fan shown in FIG. 4, enlarged sufficiently to illustrate a coating applied to an impeller vane and other surfaces within a cavity of the particles impactor;

FIG. 6 is a schematic sectional view of another embodiment of the present invention in which a vortex flow of fluid is induced within a cavity; and FIG. 7 is a schematic cut-away view of yet another embodiment in which a combined helical vane impact collector and impeller is included.

DESCRIPTION OF THE PREFERRED EMBODIMENT

A first embodiment of a particle impactor 10 is illustrated in FIGS. 1 and 2. Particle impactor 10 includes a cylindrical shaped housing 12 formed from a metal, or alternatively, molded or otherwise formed from a relatively lightweight polymer material. Housing 12 defines an internal cylindrical cavity 14. Cavity 14 is covered with a plate 16 that is held in place by a plurality of threaded fasteners 18, which pass through orifices 19 in plate 16 and are then threaded into blind threaded openings 21. Openings 21 are spaced apart around the top surface of the underlying cylindrical portion of housing 12. An O-ring 23 is seated in this top surface adjacent to blind threaded openings 21 and provides a seal against the under surface of plate 16.

A combined impact collector and fan 20 is rotatably mounted within cavity 14. Combined impact collector and fan 20 includes a round plate 22 on which are formed a plurality of impeller vanes 24, spaced apart around the top surface of plate 22 and disposed at an angle so as to serve both as a centrifugal fan that moves air into cavity 14 from an external ambient environment surrounding impact collector 10 and as an impactor on which particulates are separated from the air drawn into the cavity. Impeller vanes 24 are thus curved, so that when plate 22 is rotated, the impeller vanes draw air through an opening 28 formed in an annular plate 26 that is affixed over the top of impeller vanes 24, moving the air in which particulates are entrained from the ambient environment into cavity 14 and collecting the particulates. Specifically, in addition to drawing air (or other gaseous fluid) into cavity 14, impeller vanes 24 also impact against particulates, thus separating the particulates from the air drawn into the cavity by a least temporarily retaining the particulates on the surfaces of the impeller vanes on which the particulates have impacted. Furthermore, particulates are also collected on other surfaces within the cavity on which the particulates impact, including for example, the surfaces of plate 22, annular plate 26, and an inner surface 74 of cavity 14. Clearly, the greater the mass of the particulates, the more likely it will be that they will be separated from air or another gaseous fluid by the impact collector. However, even sub-micron particulates (including solids or semi-solids) can be separated from a gaseous fluid with the present invention, for the reasons explained below.

It should be pointed out that no additional fan or device is required to cause air or other fluid in which particulates are entrained to move into cavity 14. In virtually every other type of impact collector incorporating a rotating arm intended to separate particulates from a gaseous fluid as a result of the impact of the particulates against the rotating surface, a separate fan assembly is required to move the gaseous fluid into the vicinity of the rotating arm assembly. In contrast to such prior art devices, the present invention includes combined impact collector and fan 20, which both draws air or other gaseous fluid into the cavity and impacts the particulates to separate them from the air or other gaseous fluid in which they are entrained.

While other types of materials can be used, combined impact collector and fan 20 is preferably fabricated from a plastic material or other types of lightweight, low angular momentum or low inertia materials, to facilitate its rotation. Annular plate 26 is preferably adhesively attached to the tops of impeller vanes 24. Plate 22 is attached to a drive shaft 72 with a threaded fastener 73 that extends down through the center of plate 22 into the end of the drive shaft. A mounting plate 30 rests on the top of a plurality of standoffs 32 and includes an annular skirt 30a that depends downwardly from the perimeter of the mounting plate.

A threaded drain port 36 is provided in a bottom 34 of cavity 14 and is disposed adjacent a periphery of the cavity. During usage of particle impactor 10, a receiver 38 is threaded into threaded drain port 36 and is provided with mating threads 40 around its inlet to facilitate its rapid attachment and removal from housing 12. It is alternatively contemplated that the receiver may be held in place with a quick-release fastener (not shown) or by any other suitable mechanism, including a friction fit using an elastomeric fitting that is disposed around the neck of the receiver. Receiver 38 serves as a reservoir and includes a side arm 42 through which part of the air or other gaseous fluid that flows from cavity 14 is exhausted after the particulates entrained therein have been separated by impact with impeller vanes 24 or other surfaces within the cavity. As will be evident from the dash lines shown extending past each side of a motor 70, most of the air or other gaseous fluid flows between annular skirt 30a and a hub 35 formed in the center of the bottom of the cavity, and then exits the cavity around motor 70, thereby providing cooling for the motor.

An outlet port 44 is included in receiver 38, adjacent its bottom, and is connected through a flexible tube 46 to an inlet 48 of a centrifugal pump 50. As will be apparent from the embodiments discussed below, a peristaltic (or other type) pump may be employed instead of the centrifugal pump shown in FIGS. 1 and 2. It has been contemplated (but not shown in the drawing figures) that a Venturi pump might be fitted into an opening 60 so that the velocity of the air or other gaseous fluid drawn into cavity 14 would create a sufficiently low pressure in a Venturi tube to draw liquid from reservoir 38. This liquid would be injected into the air or gaseous fluid entering the cavity, using much the same method that is used for mixing gasoline with the air entering a cylinder in automotive carburetors. Use of such a Venturi device would enable centrifugal pump 50 to be eliminated, but would also eliminate a three-way valve 53, since the flow of liquid from the reservoir induced by a Venturi effect cannot readily be redirected through a three-way valve.

Figure 2:
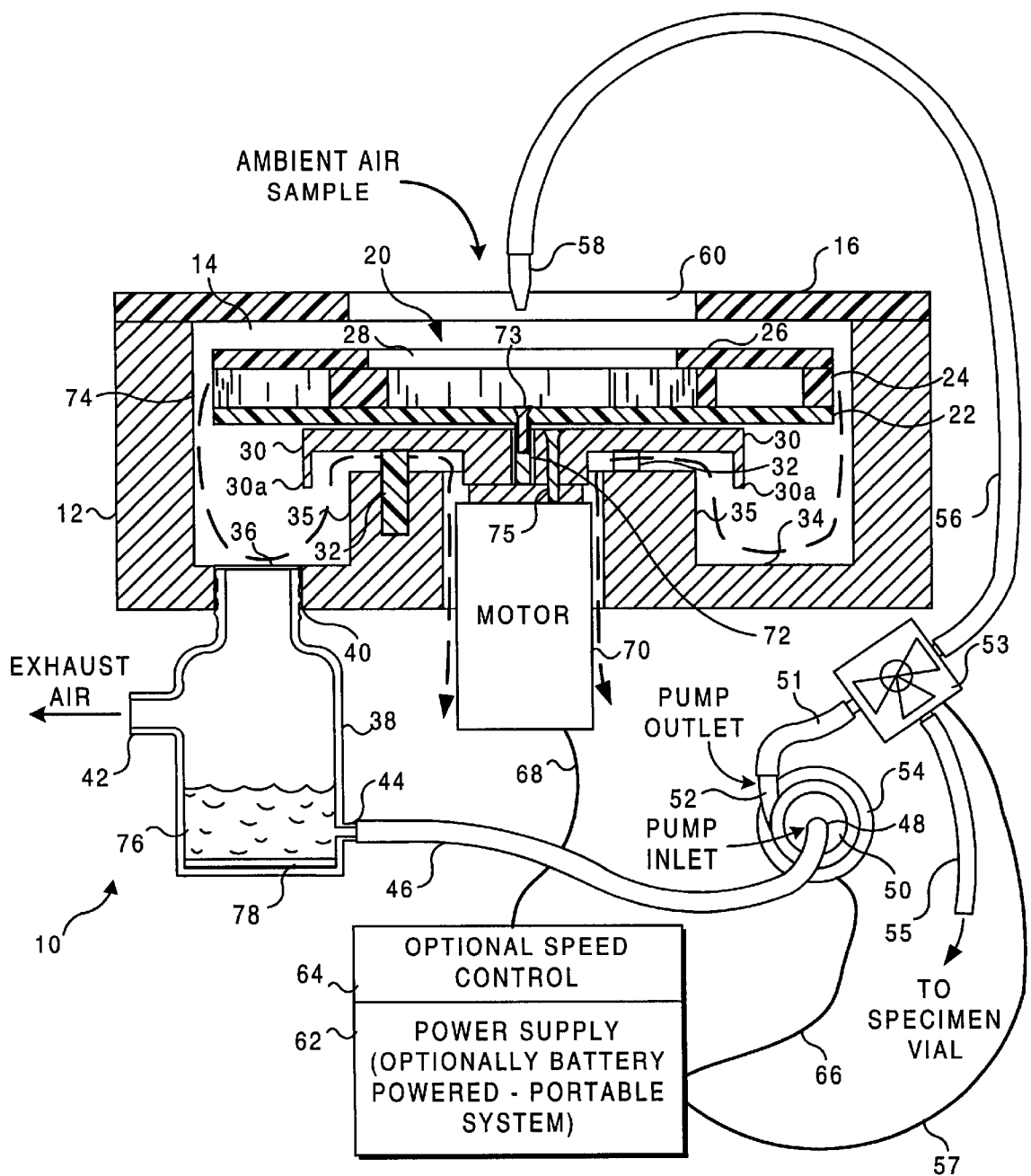

In the embodiment shown in FIGS. 1 and 2, centrifugal (or other type) pump 50 is driven by a separate motor 54. The centrifugal pump includes an outlet 52 that is connected to a flexible conduit 51. The other end of flexible conduit 51 is connected to three-way valve 53, which is controlled with an electrical signal. A flexible conduit 56 connects one outlet port of three-way valve 53 to a nozzle 58, which is disposed above inlet port 60 in cover plate 16. Liquid flowing from nozzle 58 is directed through inlet port 60 toward opening 28 in the combined impact collector and fan that is mounted within cavity 14. Nozzle 58 creates a stream of a liquid 76 that is contained within the reservoir provided by receiver 38. The liquid forms droplets that are carried by air drawn into opening 28 and these droplets wash over the surfaces of impeller vanes 24 and other surfaces within cavity 14, carrying the particulates that have been temporarily retained thereon away. The particulates are carried by the liquid down inner surface 74 toward bottom 34 of cavity 14.

Another outlet port of three-way valve 53 is connected to a flexible conduit 55, which is directed toward a specimen vial or other specimen collection container (not shown) The three-way valve can be selectively actuated by an operator to direct liquid flowing from centrifugal pump 50 into either flexible conduit 56 for circulation back into cavity 14, or into flexible conduit 55 for withdrawal of a specimen of the particulates being collected. Further options for recovering a specimen of the particulates collected are discussed below.

In addition to clearing particulates from the surfaces on which they have impacted, the liquid directed into cavity 14 through nozzle 58 also serves to entrain sub-micron particulates carried by the air or gaseous fluid that is drawn into the cavity in droplets. The entraining droplets have substantially greater mass than the sub-micron particulates alone and are thus more readily separated from the air or other gaseous fluid by impact against surfaces within cavity 14. These sub-micron particulates are thereafter carried into receiver 38, as described above.

The liquid carrying the particulates that were previously separated from the air or other gaseous fluid drawn into cavity 14 flows through threaded drain port 36 in bottom 34 of the cavity and into receiver 38. Over time, if the particulates separated from the air are solid or semi-solids and if they are denser than the liquid in the reservoir, a residue 78 of the particulates that have been collected will accumulate in the bottom of receiver 38 as the particulates settle out of the liquid. This residue can be readily removed for analysis or other tests. In other instances, where the particulates entering inlet port 60 is liquid aerosol that is miscible in liquid 76 (i.e., the liquid injected to wash the particulates from the impeller vanes), or is less dense than that liquid in the reservoir, the particulates washed from the impeller vanes will continue to increase in concentration within liquid 76, forming a readily collected specimen of the particulates within the reservoir. When this specimen is analyzed, the chemical composition of the aerosols or materials comprising the particulates can be readily determined. It is also noted that the particulates drawn into the impact collector may comprise bacteria or spores, which are also readily analyzed. A sample of liquid 76, with the particulates contained therein comprising a specimen are readily withdrawn from receiver 38 by actuating three-way valve 53 so that it pumps the specimen from the receiver and empties flexible conduit 46 into a specimen vial through flexible conduit 55.

Once the receiver has been emptied, a sterilant or disinfecting solution such as hydrogen peroxide solution, may be circulated through the impact collector from receiver 38, using centrifugal pump 50. Use of the sterilizing solution would then be followed by several rinses to prepare the impact collector to receive another specimen.

It is contemplated that a small heating element (not shown) may be provided either around, adjacent to, or inside the receiver to ensure that liquid 76 does not freeze. Provision of such a heating element should be necessary only if the device is exposed to an ambient temperature that is below the freezing point of the liquid in the receiver.

To rotate the combined impact collector and fan 20, motor 70 is provided. The motor is connected to mounting plate 30 using a plurality of threaded fasteners 75 (only one of which shown in FIG. 2). As noted above, drive shaft 72 of motor 70 is connected to plate 22 using threaded fastener 73. Although not shown, drive shaft 72 may also include a spline, or a flat surface against which a set screw can be tightened to ensure that the combined impact collector and fan is rotatably driven by drive shaft 72 when motor 70 is energized.

A power supply and pump/valve control 62 provides electrical current for energizing pump motor 54 and motor 70. The position of three-way valve 53 is controlled by the operator using power supply and pump/valve control 62. The electrical current supplied to pump motor 54 is conveyed through a power lead 66. Optionally, a speed control 64 is included to enable an operator to selectively control the speed of motor 70. In a preferred embodiment, motor 70 is a Micromole Inc. brushless DC motor, Series 1628, although other similar types of motors are equally usable for this purpose. Optional speed control 64 can be used to adjust the rotational speed of motor 70, and thus to enable the rotational speed of the combined impact collector and fan to be set within the range of about 80 to 50,000 rpm (or greater if a motor capable of higher speed is used). The specified speed range corresponds to a rate of fluid flow through the impact collector of 80 liters per minute to 540 liters per minute. Substantially higher flow rates may be required for specific applications of the flow impactor. Generally, it is preferable to operate the impact collector at a higher rotational speed, since it has been determined that the efficacy of particulate collection improves with increased rotational speed of the combined impact collector and fan. While optional speed control 64 may provide for continuously variable speed within the range of motor 70, it is more likely that a multi-position switch would be provided to select the desired speed, for example, from a low, medium, or high speed option.

Figure 3:
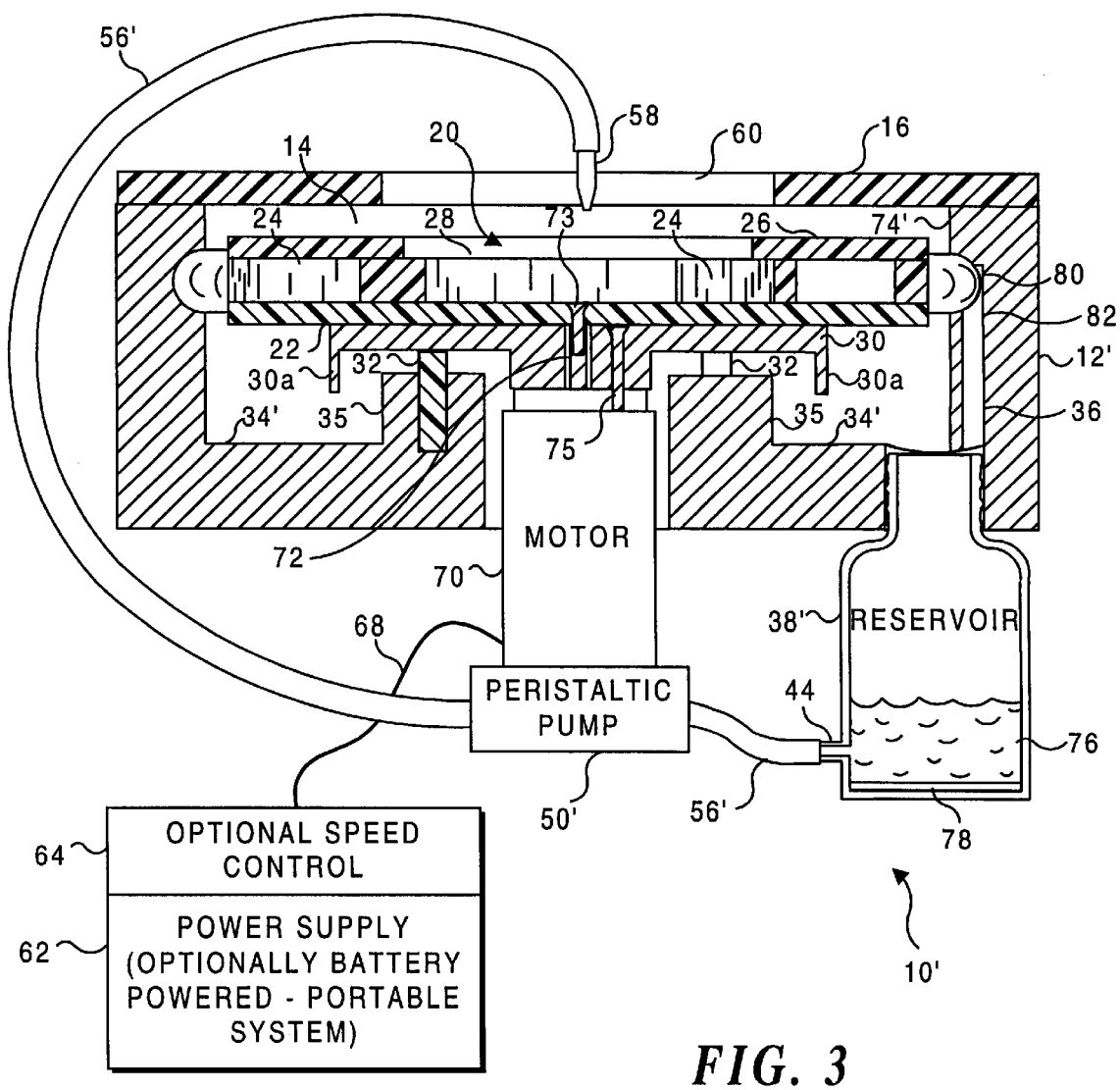

FIG. 3 illustrates a second embodiment of an impact collector 10', which is generally similar in its operation to that of the first embodiment. Accordingly, identical reference numerals have been used for each of the elements of the second embodiment shown in FIG. 3, except where slight differences exist in the configuration or manner of operation discussed above in connection with the first embodiment. Impact collector 10' includes a housing 12' in which an annular groove 80 is formed around an inner surface 74' of the cavity defined by the housing, immediately adjacent the peripheral edge of combined impact collector and fan 20. At spaced-apart intervals around annular groove 80, vertical passages 82 are provided for conveying liquid carrying particulates washed from impeller vanes 24 downwardly toward a bottom 34' of cavity 14. Bottom 34' includes a depression around its peripheral extent, thereby encouraging the liquid that is carrying the particulates washed from the combined impact collector and fan to flow into a receiver 38', which does not include side arm 42, as was the case with receiver 38 in FIGS. 1 and 2. In the embodiment shown in FIG. 3, all of the air or other gaseous fluid exhausted from cavity 14 flows out around motor 70.

A further difference between the first and second embodiments is that motor 70 also provides the rotational driving force for a peristaltic pump 50' that is coupled to the lower end of the motor. Peristaltic pump 50' draws liquid from the reservoir within receiver 38 and recirculates it through flexible conduit 56 back into cavity 14. By avoiding the need for a separate pump motor for peristaltic pump 50', a relatively lower cost and a more compact configuration is achieved for impact collector 10', compared to impact collector 10. Also, peristaltic pump 50' can be reversed by reversing the direction of rotation of motor 70, so that all of the liquid within flexible conduit 56' can be returned into reservoir 38' before the specimen of particulates collected with the liquid in the reservoir is removed for analysis or other study.

Figure 4:
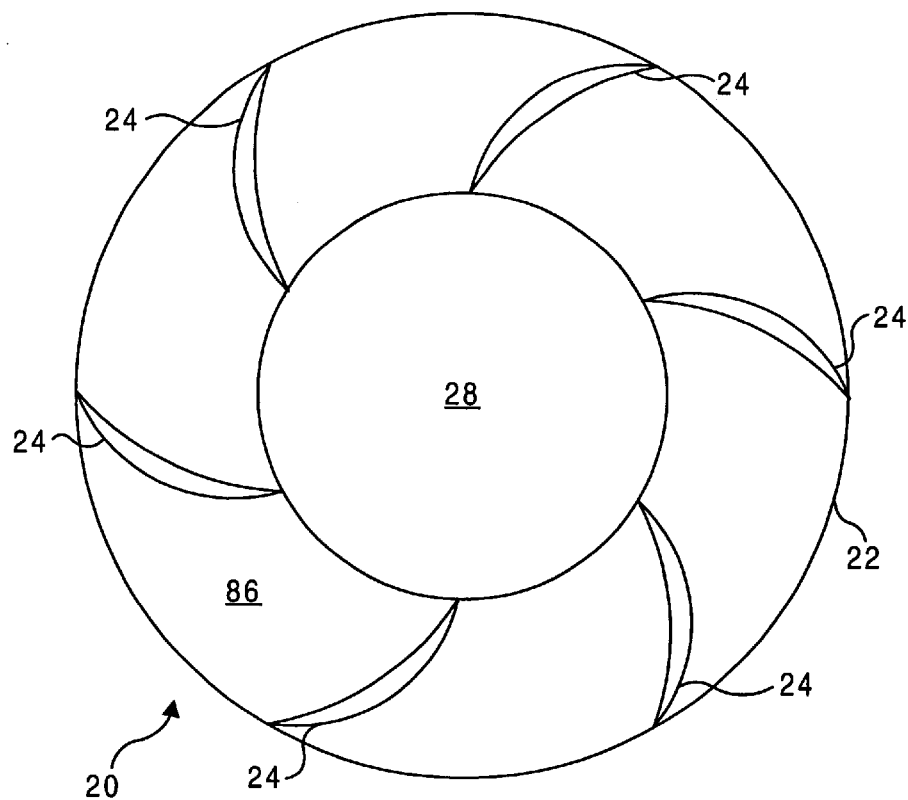
Figure 5:
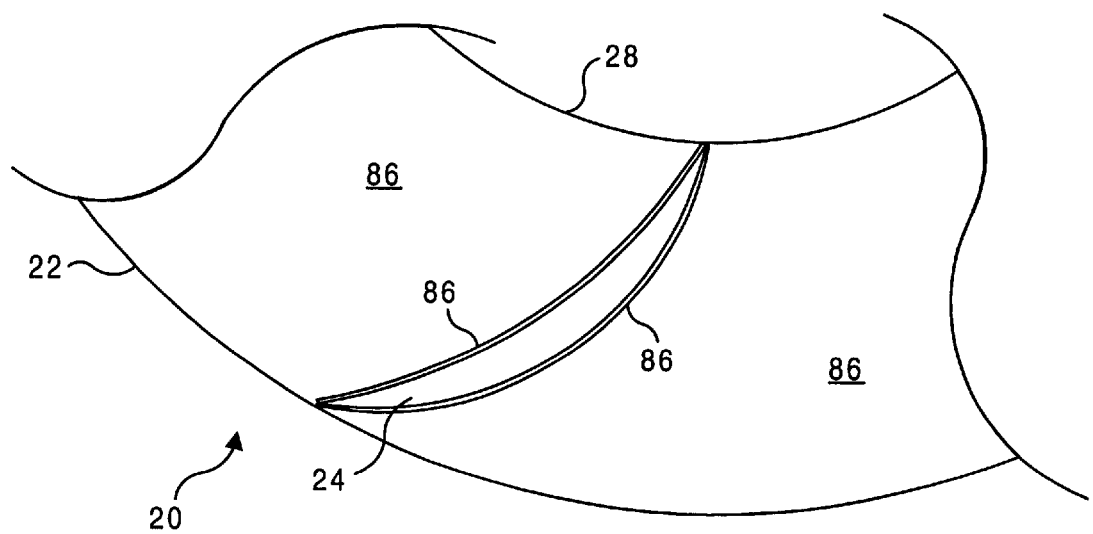

Further details of the combined impact collector and fan are illustrated in FIGS. 4 and 5. As shown in FIG. 5, a coating 86 has been applied to the exposed surfaces of each impeller vane 24 and of plate 22. In addition, coating 86 is preferably applied to all exposed surfaces within the cavity of the impact collector—in all of the embodiments disclosed herein. Two types of coatings 86 are contemplated. The first type of coating is identified as a substance called TETRAGLYME. This substance is hydrophilic until it is exposed to water and when dry, is relatively very sticky, tending to readily retain particulates that impact the surfaces of impeller vanes 24 that are coated with the substance. However, once water is sprayed into opening 28 and wets the TETRAGLYME coating, it becomes hydrophobic, is no longer sticky or tacky, and in fact, readily releases the particulates that previously were retained by it. The water washes the particulates from coating 86 and carries the particulates down into receiver 38, as described above.

A second type of material being considered for coating 86 is PARYLENE, which is a tetrafluoromore manufactured and sold by Dupont Chemical Company under the trademark INSUL-COTE™, Type N, and is characterized by a relatively low coefficient of friction causing it to be extremely slippery and not sticky. Accordingly, particulates impacting against coating 86 comprising PARYLENE are separated from the gaseous fluid in which they are carried and are immediately washed away by water or other liquid injected through opening 28. It is expected that further empirical testing will determine which of these two coatings provides the maximum efficacy for separating particulates from air or other gaseous fluid entering inlet port 60 using combined impact collector and fan 20.

With reference to power supply 62, it is contemplated that it will be desirable to produce a readily portable impact collector. Accordingly, power supply 62 may be powered by one or more batteries (not separately shown), thereby enabling the impact collector to be readily hand carried in the field for use in collecting samples from ambient air or from other sources of gaseous fluids in which particulates are entrained. For example, samples from smokestack emissions may be collected using such a portable device. In addition, a portable impact collector in accord with the present invention will be useful in collecting air samples for use in detecting deployment of and identifying chemical and biological warfare weapons, since such samples can be used for sensing the presence of toxic chemicals and undesirable bacteria, and also can be analyzed to identify these substances.

During operation of the present invention, it is contemplated that either of two modes may be employed for circulating liquid from receiver 38 into cavity 14. In a first mode, liquid from the reservoir within receiver 38 is continuously circulated during rotation of the combined impact collector and fan. Impact collector 10' is particularly adapted to employ this mode of operation, since motor 70 rotates both the combined impact collector and fan, and peristaltic pump 50'. In the second mode, liquid is periodically injected into cavity 14 after particulates have collected on the surface of impeller vanes 24 and on the other surfaces within cavity 14 to which coating 86 is applied; the liquid washes the particulates from the impeller vanes and other surfaces, such as the inner wall of the cavity. Impact collector 10 is better adapted to employ this mode of operation, since pump motor 54 and motor 70 can be separately controlled. Furthermore, it is apparent that coating made from TETRAGLYME is preferable for use in connection with the second mode of operation, since the coating needs to dry out to become sticky and better retain particulates that have impacted the coating on the rotating impeller vanes. After being thus separated from the air or other gaseous fluid, the particulates should then be washed from the coating, which when wetted by water, readily release the particulates so that they flow with the water into the reservoir.

Figure 6:
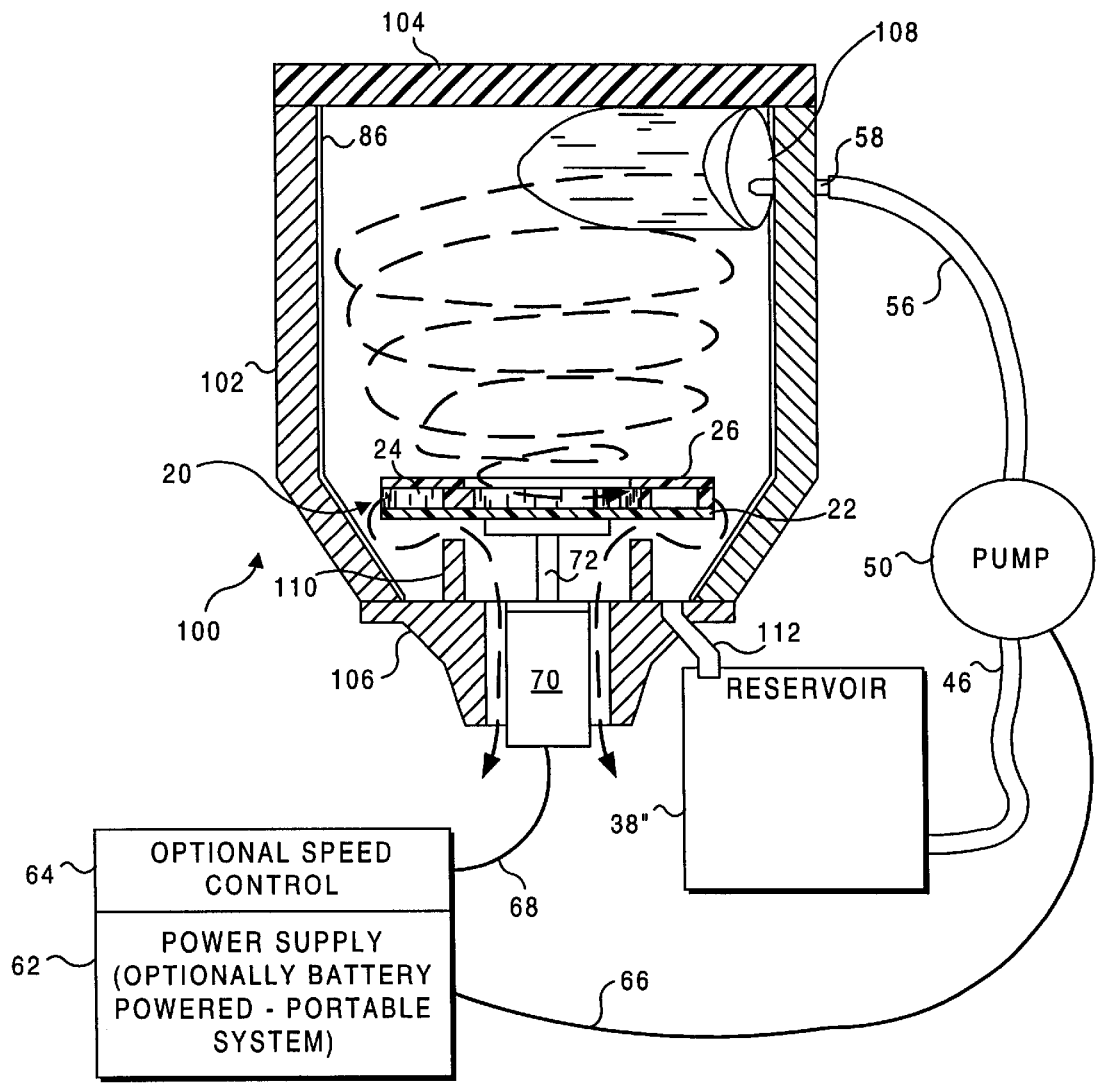

Another embodiment of an impact collector 100 in accord with the present invention is shown in a schematic representation in FIG. 6. In impact collector 100, an upper housing 102 is formed in a shape that encourages a vortex to be created in the air or other gaseous fluid entering the cavity of the housing. A cover 104 closes one open end of the upper housing, and a lower housing 106 is sealingly attached to the lower depending end of upper housing 102.

Adjacent cover 104 is formed a tangential opening 108 through upper housing 102. Air or other gaseous fluid is drawn into the cavity of impact collector 100 through this tangential opening by rotation of combined impact collector and fan 20, which is mounted on shaft 72 of motor 70. As in the previous embodiments, rotation of shaft 72 causes combined impact collector and fan 20 to rotate, which draws the air or other gaseous fluid into the cavity of the upper housing. However, this embodiment provides a much greater wetted surface area on the inner surface of upper housing 102 against which particulates impact as the gaseous fluid rotates in a vortex. The inner surface of the upper housing and other surfaces within the cavity are coated with coating 86 to promote the separation and collection of particulates from the air or gaseous fluid, generally as discussed above. Particulates also impact on vanes 24 of the combined impact collector and fan and are retained there until washed away by liquid pumped from a reservoir 38" by pump 50. A dam 110 tends to retain the liquid carrying the particulates that have been washed from the surfaces so that the liquid flows into reservoir 38" through a conduit 112. While not illustrated in this embodiment, it will be apparent that the three-way valve can also be used to facilitate taking a specimen from the liquid in reservoir 38". Air or other gaseous fluid exhausts from the interior of impact collector 100 past motor 70, as indicated by the dash arrows.

Figure 7:
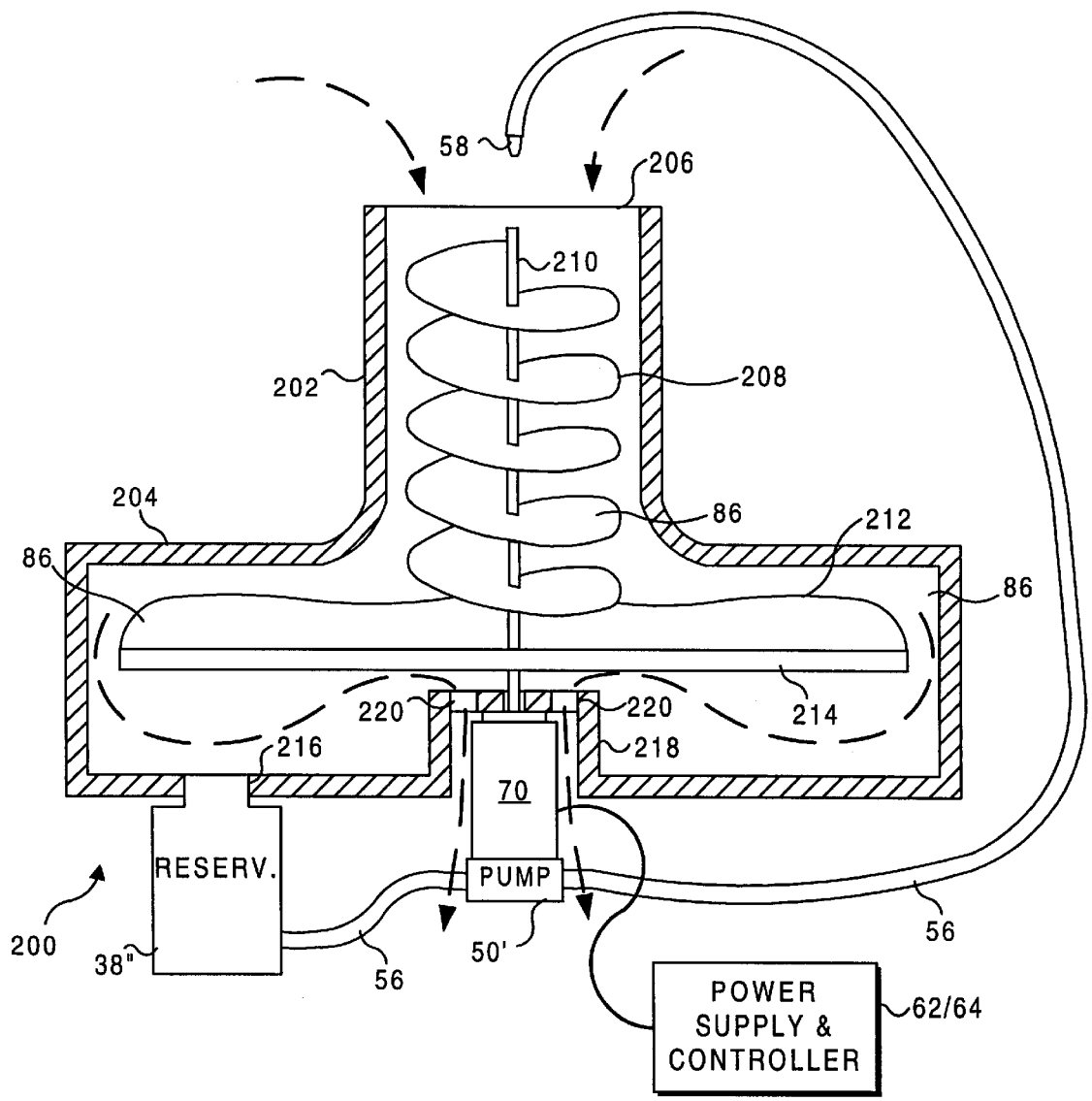

Yet another embodiment of an impact collector 200 is illustrated in FIG. 7. This embodiment is also represented in a schematic manner and is included as provide an example of a different configuration for the combined impact collector and fan. A helical vane portion 208 of the combined impact collector and fan extends upwardly within a housing throat 202. The housing throat has a substantially smaller diameter than a lower housing 204 in which a plurality of impeller vanes 212 are disposed. The impeller vanes are mounted on a round plate 214, which is rotatably driven by a shaft 210 of motor 70. Air or other gaseous fluid in which particulates are entrained enters through an opening 206 at the top of housing throat 202, drawn by the rotation of helical vanes 208 and impeller vanes 212. The particulates impacting upon the surfaces of these vanes and on the interior surfaces of the throat housing and the lower housing are separated from air or other gaseous fluid. This air or other gaseous fluid exhausts through port 220 and flows past motor 70, cooling it.

As in the embodiment of FIG. 3, motor 70 drives a peristaltic (or other type) pump 50', which circulates water or other liquid from reservoir 38" through flexible conduit 56 and into opening 206 through nozzle 58. The liquid washes the particulates from coating 86, which covers the surfaces of the helical vanes and impeller vanes and other surfaces, including the inner surfaces of housing throat 202 and lower housing 204. The liquid carrying the particulates washed from these surfaces flows into reservoir 38" through an opening 216 formed in the bottom of lower housing 204. A hub 218 around motor 70 prevents the liquid inside the cavity from flowing through port 220 with the air or other gaseous fluid.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. An impact particle collector for separating particulates from a gaseous fluid in which the particulates are entrained, comprising:

(a) a prime mover having a drive shaft that is drivingly rotated;

(b) an impeller that is mechanically coupled to the drive shaft and rotated thereby; and (c) a housing for the impeller, said housing defining a fluid passage for conveying the gaseous fluid in which the particulates are entrained to the impeller, said impeller including vanes that draw the gaseous fluid into the housing so that the particulates entrained in the gaseous fluid impact upon the impeller, being thereby separated from the gaseous fluid when impacted by the vanes of the impeller.

2. The impact particle collector of claim 1, further comprising a liquid conduit that conveys a liquid into the housing and onto the impeller, said liquid washing the particulates that have been separated from the gaseous fluid from the vanes of the impeller.

3. The impact particle collector of claim 2, wherein the liquid comprises water.

4. The impact particle collector of claim 2, wherein the impeller is coated with a substance to which the particulates adhere when the substance is dry, said substance releasing the particulates when wetted with the liquid.

5. The impact particle collector of claim 2, wherein an inner surface of the housing is wetted by the liquid to wash away the particulates that become separated from the gaseous fluid.

6. The impact particle collector of claim 2, further comprising a passage through the housing through which the liquid and the particulates washed from the vanes of the impeller by the liquid are conveyed.

7. The impact particle collector of claim 6, further comprising a receiver coupled in fluid communication with the passage, said receiver collecting the particulates and the liquid.

8. The impact particle collector of claim 7, wherein the particulates comprise at least one of a solid and a semi-solid matter.

9. The impact particle collector of claim 7, wherein the particulates comprise droplets, and wherein over time as the droplets are impacted on the impeller, a concentration of a matter comprising the droplets becomes greater in the liquid within the receiver than within the gaseous fluid carrying the particulates that was drawn into the housing.

10. The impact particle collector of claim 7, further comprising a pump that draws the liquid from the receiver and forces it back into the housing through the liquid conduit.

11. The impact particle collector of claim 10, wherein the pump is driven by the prime mover.

12. The impact particle collector of claim 1, wherein the gaseous fluid comprises air that is sampled from an ambient environment.

13. The impact particle collector of claim 1, wherein a plurality of surfaces within the housing are coated with a substance that facilitates separation and collection of the particulates that have impacted said plurality of surfaces.

14. The impact particle collector of claim 13, wherein the substance used for coating the plurality of surfaces is characterized by having a low coefficient of friction so that the particulates readily slide off the plurality of surfaces on which they have impacted.

15. Apparatus for separating particulates from a fluid, comprising:
   (a) a housing defining a port through which the fluid carrying the particulates passes;
   (b) an electrically energizable motor that rotates a drive shaft; and
   (c) a combined impact collector and fan mechanically coupled to the drive shaft and rotated thereby, said combined impact collector and fan being disposed within a cavity defined by the housing, rotation of the combined impact collector and fan drawing the fluid into the cavity of the housing through the port, the particulates in the fluid impacting the combined impact collector and fan and being retained thereon and being thus separated from the fluid.

16. The apparatus of claim 15, further comprising a conduit that conveys a liquid into the cavity of the housing, said liquid being directed toward the combined impact collector and fan and washing the particulates from the combined impact collector and fan.

17. The apparatus of claim 16, wherein the combined impact collector and fan includes a coating to which the particulates adhere when the coating is dry, said coating releasing the particulates when wetted with the liquid.

18. The apparatus of claim 16, wherein the combined impact collector and fan includes a coating characterized by having a low coefficient of friction, said particulates sliding off the combined impact collector and fan due to a centrifugal force when wetted by the liquid.

19. The apparatus of claim 16, further comprising a collection channel formed in the housing to collect the particulates and liquid thrown from the combined impact collector and fan toward an interior surface that is adjacent a periphery of the combined impact collector and fan.

20. The apparatus of claim 19, further comprising a receiver coupled in fluid communication with the collection channel, said liquid washing the particulates from the combined impact collector and fan, so that the particulates and the liquid are radially dispersed onto the interior surface of the housing and then flow through the collection channel into the receiver.

21. The apparatus of claim 20, wherein the particulates comprise droplets, a concentration of a matter comprising the droplets becoming greater in the liquid within the receiver than within the fluid drawn into the cavity, over time.

22. The apparatus of claim 20, wherein the particulates comprise at least one of a solid and a semi-solid.

23. The apparatus of claim 20, further comprising a pump that draws the liquid from the receiver and circulates it back into the cavity of the housing through the conduit.

24. The apparatus of claim 23, wherein the pump operates intermittently while the electrically energizable motor is rotating the combined impact collector and fan.

25. The apparatus of claim 23, wherein the pump is mechanically coupled to the shaft of the electrically energizable motor and is driven thereby.

26. The apparatus of claim 15, further comprising a power supply for providing an electrical current to energize the electrically energizable motor.

27. The apparatus of claim 26, wherein the power supply includes a battery that produces the electrical current, said power supply and said housing being portable and sufficiently small in size and weight to be readily hand carried.

28. A method for separating particulates from a fluid, comprising the steps of:
   (a) providing a combined impact collector and fan disposed within a cavity having a port, said combined impact collector and fan being rotatable about an axis;
   (b) rotating the combined impact collector and fan about the axis;
   (c) drawing the fluid carrying the particulates into the cavity by causing the combined impact collector and fan to rotate; and
   (d) separating the particulates from the fluid by impacting them with the combined impact collector and fan as it rotates.

29. The method of claim 28, further comprising the step of washing the particulates from the combined impact collector and fan with a liquid.

30. The method of claim 29, wherein the liquid comprises water that is directed into the cavity through a conduit.

31. The method of claim 29, further comprising the step of coating surfaces within the cavity with a material that facilitates separation of the particulates from the fluid and collection of the particulates.

32. The method of claim 31, wherein adherence of the particulates to the material changes when the material is wetted with the liquid.

33. The method of claim 29, further comprising a step of emptying a line carrying the liquid to obtain the particulates within the liquid.

34. The method of claim 29, further comprising the step of collecting a sample of the particulates carried away by the liquid.

35. The method of claim 29, further comprising the steps of collecting the liquid and the particulates in a receiver.

36. The method of claim 35, further comprising the step of circulating the liquid from the receiver to wash the particulates from the combined impact collector and fan.

37. The method of claim 29, further comprising the step of enabling the particulates to settle out from the liquid.

38. The method of claim 29, wherein the particulates comprise droplets, further comprising the step of increasing a concentration of a matter comprising the droplets within the receiver as the method is carried out over time.

39. The method of claim 29, further comprising the step of providing the combined impact collector and fan with a coating to which the particulates adhere when the coating is dry, and which releases the particulates when the coating is wetted with the liquid.

40. The method of claim 29, further comprising the step of providing the combined impact collector and fan with a coating that is characterized by having a low coefficient of friction so that the particulates readily slide off the coating.

41. The method of claim 28, wherein the fluid comprises air, further comprising the step of drawing air carrying the particulates into the cavity with the combined impact collector and fan from an ambient environment.

42. The method of claim 28, wherein the particulates comprise organic material.

\* \* \* \* \*